United States Patent
Kaladelfos (10) Patent No.: US 6,494,887 B1
(45) Date of Patent: Dec. 17, 2002

(54) SURGICAL INSTRUMENT

(76) Inventor: George Kaladelfos, 17 Brighton Avenue, Toronto, New South Wales 2283 (AU)

( * ) Notice: Subject to any disclaimer, the term of this patent is extended or adjusted under 35 U.S.C. 154(b) by 42 days.

(21) Appl. No.: 09/692,332

(22) Filed: Oct. 19, 2000

(30) Foreign Application Priority Data

Oct. 22, 1999 (AU) .............................................. PQ3621

(51) Int. Cl.⁷ .......................... A41B 17/04; A41B 19/00
(52) U.S. Cl. ...................... 606/148; 606/119; 606/139; 606/185; 606/128; 606/898; 606/DIG. 25
(58) Field of Search .................. 606/119, 148, 606/185, 139; 600/30; 604/272; 128/898, DIG. 25

(56) References Cited

U.S. PATENT DOCUMENTS

| | | | |
|---|---|---|---|
| 4,643,178 A | * | 2/1987 | Nastari et al. ............... 606/103 |
| 5,013,292 A | * | 5/1991 | Lemay ......................... 600/30 |
| 5,112,344 A | * | 5/1992 | Petros ................. 128/DIG. 25 |
| 5,207,694 A | * | 5/1993 | Broome ..................... 24/16 PB |
| 5,234,438 A | * | 8/1993 | Semrad ....................... 604/264 |
| 5,350,385 A | * | 9/1994 | Christy ........................ 606/139 |
| 5,382,257 A | * | 1/1995 | Lewis et al. ................. 606/148 |
| 5,562,685 A | * | 10/1996 | Mollenauer et al. ......... 112/169 |
| 5,647,836 A | * | 7/1997 | Blake et al. .................... 600/30 |
| 5,788,679 A | * | 8/1998 | Gravlee, Jr. .................... 604/22 |
| 5,830,220 A | * | 11/1998 | Wan et al. .................... 128/898 |
| 5,928,250 A | * | 7/1999 | Koike et al. ................. 606/139 |
| 5,935,138 A | * | 8/1999 | McJames et al. ............ 606/139 |
| 6,273,852 B1 | * | 8/2001 | Lehe et al. ........... 128/DIG. 25 |

FOREIGN PATENT DOCUMENTS

DE 4114204 A1 * 11/1992 ............ A61B/17/06

* cited by examiner

Primary Examiner—Rodney M. Lindsey
(74) Attorney, Agent, or Firm—Gottlieb, Rackman & Reisman, P.C.

(57) ABSTRACT

The invention provides a surgical instrument for inserting an elongate element into a human patient. In the preferred form of the invention the instrument has a curved hollow shaft defining an arc corresponding to the general curvature of a passage between the anterior vaginal wall and the abdomen of a female patient and having a cutting tip at one end and a handle at the other end. An elongate threading element is used draw a filamentary element through the shaft. Once the filamentary element is in position the shaft is removed from the patient, leaving the element in position. The instrument is preferably used to insert a U-shaped loop of filamentary material into the patient which passes around the patient's urethra and helps the patient improve her urinary control.

33 Claims, 8 Drawing Sheets

SURGICAL INSTRUMENT

FIELD OF THE INVENTION

The present invention relates to a surgical instrument for a method of placing elongate elements in a patient, more particularly, but not exclusively in the field of obstetrics and gynaecology and more particularly the invention relates to an apparatus and method for the treatment of female urinary incontinence.

BACKGROUND OF THE INVENTION

Female incontinence generally occurs due to deterioration of or damage to muscle tissue and ligaments in the pelvic region. This results in involuntary leakage of urine from the urethra due to lack of control of the patient's pelvic muscles, particularly the urogenital diaphragm and pubo urethral ligaments. It has been found that the condition can be treated by creating some form of artificial ligament between the abdominal muscles and the urethra, the ligament passing behind the pubis.

The application is aware of two prior art patents which deal with similar subject matter to that of this invention, namely U.S. Pat. No. 5,112,344 (Petros) and U.S. Pat. No. 5,899,909 (Claren). U.S. Pat. No. 5,112,344 describes a method and apparatus for treating female incontinence. The surgical instrument for the application of a filamentary element into the body comprises a tubular shaft having a handle at one end and a flexible needle slidably receivable in the shaft and adapted at one end to receive a filamentary element. The method of treating female incontinence comprises looping a filamentary element between the wall of the vaginal and the rectus abdominis sheath in the anterior wall of the abdomen whereby it masses to each side of the urethra, adjusting the loop to bring the vaginal wall and the urethra into the correct spatial relationship to the pubis allowing the development of scar tissue between the vaginal wall and the anterior wall of the abdomen pubic symphysis and removing the filamentary element.

The Claren Patent, U.S. Pat. No. 5,899,909, also describes a surgical instrument and a method for treating female urinary incontinence. The instrument comprises a shank having a handle at one end thereof, and two curved needle-like elements which are connected at one end thereof each with one end of a tape intended to be implanted into the body. These elements can be connected one at a time with the shank at the other end thereof to form a curved end portion of the shank and are intended to be passed into the body via the vagina, each element being dimensioned to extend from the inside of the vaginal wall over the back of the pubic bone to the outside of the abdominal wall. When practicing the method the tape is passed into the body via the vagina first at one end and then at the other end at one side and the other, respectively, of the urethra to form a loop around the urethra, located between the urethra and the vaginal wall. The tape is extended over the pubis and through the abdominal wall and is tightened. Then, the tape ends are cut at the abdominal wall, and the tape is left implanted in the body.

SUMMARY OF THE INVENTION

In its broadest form the invention provides a surgical instrument for use in placing an elongate element into a patient said instrument comprising:

an elongate shaft defining an internal passage, said shaft having a cutting tip formed on one end thereof and handle means formed on the other end thereof, the shaft including the handle means being of substantially uniform cross-section along its entire length such that the shaft may be passed into and through a patient, the internal passage being adapted to be used to introduce a said elongate element into a patient whilst the instrument is located in a patient in use.

In one preferred form of the invention there is provided a surgical instrument for use in placing a filamentary element into a female patient so as to form a sling or loop around the urethra extending over the back of the pubic bone, to the abdominal wall, said instrument comprising:

- a generally arcuately curved tubular shaft defining an internal passage, said shaft having a cutting tip formed on one end thereof and handle attachment means formed on the other end thereof, the shaft being of substantially uniform cross-sectional diameter along its entire length;
- a handle, non-rotatably connectable to the handle attachment means of the shaft;
- a flexible threading element insertable into and through said internal passage from either end of said shaft at least when the handle is detached from the shaft and adapted to be used to draw one end of a said filamentary element through said internal passage.

According to another aspect of the invention there is provided a surgical instrument for use in placing a filamentary element into a female patient so as to form a sling or loop around the urethra extending over the back of the pubic bone, to the abdominal wall, said instrument comprising:

- a generally arcuately curved tubular shaft defining an internal passage, said shaft having a cutting tip formed on one end thereof and handle attached means formed on the other end thereof;
- a handle, non-rotatable to the shaft when connected thereto and further connectable to the handle attachment means of the shaft;
- a flexible threading element insertable into and through said internal passage from either end of said shaft and adapted to be used to draw one end of a said filamentary element through said internal passage;
- said tubular shaft being curved so that the shaft lies substantially in a single plane;
- the cutting tip being formed having a transverse angle which lies at least substantially in a plane perpendicular to said single plane and at an acute angle to the shaft axis. The leading edge of the tip preferably lies on the radially inner side of said curved tubular shaft.

The acute angle is preferably between 20° and 70° and it is more probably approximately 45°. Preferably the leading end of the shaft is curved.

The cutting tip may be formed having two bevel faces, inclined to each other at an acute angle. The two level faces preferably intersect along a line which is perpendicular to the shaft axis.

In one arrangement the handle attachment means comprises screw threads formed on the outer surface of the shaft. Preferably the shaft tapers divergently towards the handle attachment means so as to form a smooth transition between a cylindrical portion of said shaft and said handle attachment means.

An interior surface of said internal passage at or towards said other end of the shaft may include one or more notch or detent formation with which said handle will engage to provide for said non-rotatable connection.

Said handle preferably comprises a hand engageable portion which is significantly wider than said shaft and a shaft portion adapted to be axially aligned with said other end of the tubular shaft when the handle and the tubular shaft are operatively connected. Said shaft portion may have a distal end of reduced diameter adapted to be inserted into the internal passage of the shaft. Preferably the handle includes an annular flange on said shaft portion adapted to engage against said other end of said tubular shaft, and a union nut captively held on said shaft portion between the annular flange and the handle portion and slidable on said shaft portion, said union nut adapted to engage with the screw threads formed on the tubular shaft in order to hold the tubular shaft and handle together.

The tubular shaft preferably has a generally arcuate portion towards the end thereof remote from the handle end thereof, and a generally straight portion towards the handle end thereof.

The tubular shaft may have a series of apertures passing through the wall thereof between the internal passage and the exterior of the shaft, said apertures being spaced apart along the length of the shaft.

According to a further aspect of the invention there is provided a surgical instrument for use in placing a filamentary element into a female patient to form a sling or loop between an anterior surface of the vaginal wall, around the back of the pubic bone to the outside of the abdominal wall, said instrument comprising a generally curved tubular shaft defining an internal passage, said shaft having at least one aperture passing through the wall thereof between the internal passage and exterior of the shaft.

Preferably there are a series of such apertures spaced apart along the length of the shaft. Preferably the apertures are located on the convex side of the shaft. The shaft preferably has a cutting tip formed on one end thereof and handle attachment means on the other end thereof, and the shaft has a generally arcuate portion towards the end thereof remote from the handle end, and a generally straight portion towards the handle end, the apertures being located at least in the generally arcuate portion.

According to a further aspect of the invention there is provided a method of introducing a filamentary element into a female patient so as to form a sling or loop extending around the urethra to an anterior surface of the abdominal wall, said method including the steps of:

a) inserting a generally arcuately curved shaft, having a longitudinally extending internal passage, into the patient through the anterior surface of the vaginal wall, so as to pass on one side of the urethra between the pubis and the bladder and pass out of the patient through the abdominal wall;

b) passing a threading element along the internal passage from one or other end thereof so that the distal end of the threading element passes out of the remote end of the shaft;

c) attaching a filamentary element to the distal end of the threading element and drawing the filamentary element through the shaft with the threading element;

d) withdrawing the shaft from the patient whilst leaving the filamentary element in position in the patient;

e) inserting the shaft into the patient through the anterior surface of the vaginal wall, so as to pass on the other side of the urethra between the pubis and the bladder and pass out of the patient through the abdominal wall;

f) repeating steps b), c) and d) to draw the filamentary element through the shaft; and g) withdrawing the shaft from the patient whilst leaving the filamentary element in position thereby forming a loop which extends around the urethra to the anterior surface the abdominal wall on opposite sides of the urethra.

The shaft may either be tubular or U-shaped in cross section having a longitudinal slot or groove extending along the length thereof.

The aforementioned method may be performed using either a single incision or a pair of incisions. The two incisions method includes forming a pair of para-urethral incisions are made at or very near each anterior sulcus of the vagina. A tunnel is created by blunt dissection between the urethra and the vaginal wall, extending from each vaginal incision. Prior to conducting step (e) the end of the filamentary element adjacent the vagina is passed through that tunnel and out of the second of the two incisions. Step (f) is conducted through the second of the two incisions.

It will be appreciated that the process allows the threading element to be inserted into the hollow shaft from either end of the shaft, as desired.

Preferably the shaft is provided with a detachable handle, the shaft being of substantially uniform outer dimensions along its entire length thereby allowing the shaft to be withdrawn from the patient, once the handle has been removed, from the outside of the abdominal wall.

These and further features of the invention will be made apparent from the description of an embodiment thereof given below by way of example. In the description reference is made to the accompanying drawings, but the specific features shown in the drawings should not be construed as limiting on the invention.

DETAILED DESCRIPTION OF THE EMBODIMENTS

Referring to FIGS. 2 to 6 of the drawings, a surgical instrument 10 according to the invention is shown in detail.

Figures 1A, 1B:
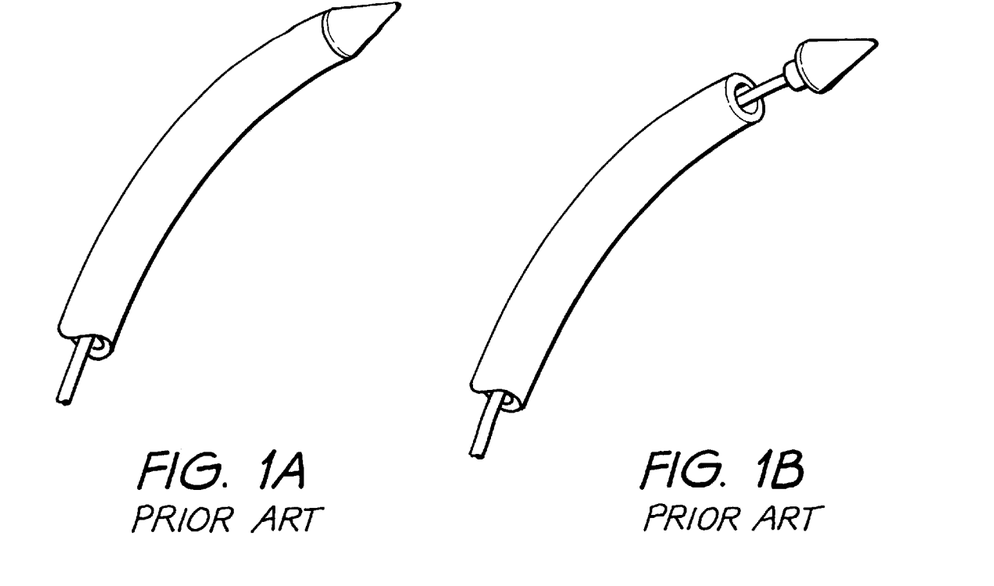
FIGS. 1A and 1B show the leading end of a prior art surgical instrument of the type described in U.S. Pat. No. 5,112,344.
Figure 2:
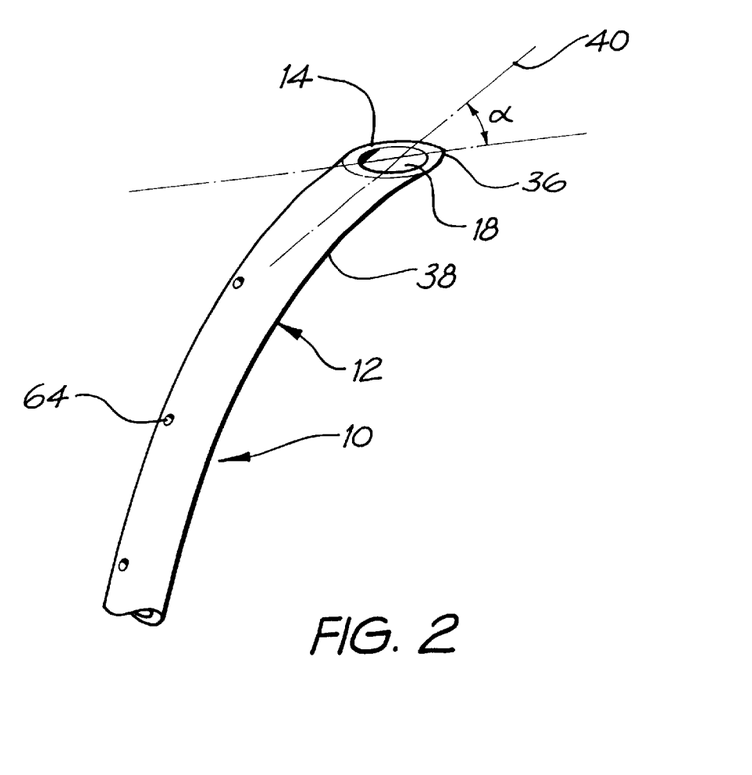
FIG. 2 shows a perspective view of the leading end of a surgical instrument according the invention.
Figure 3:
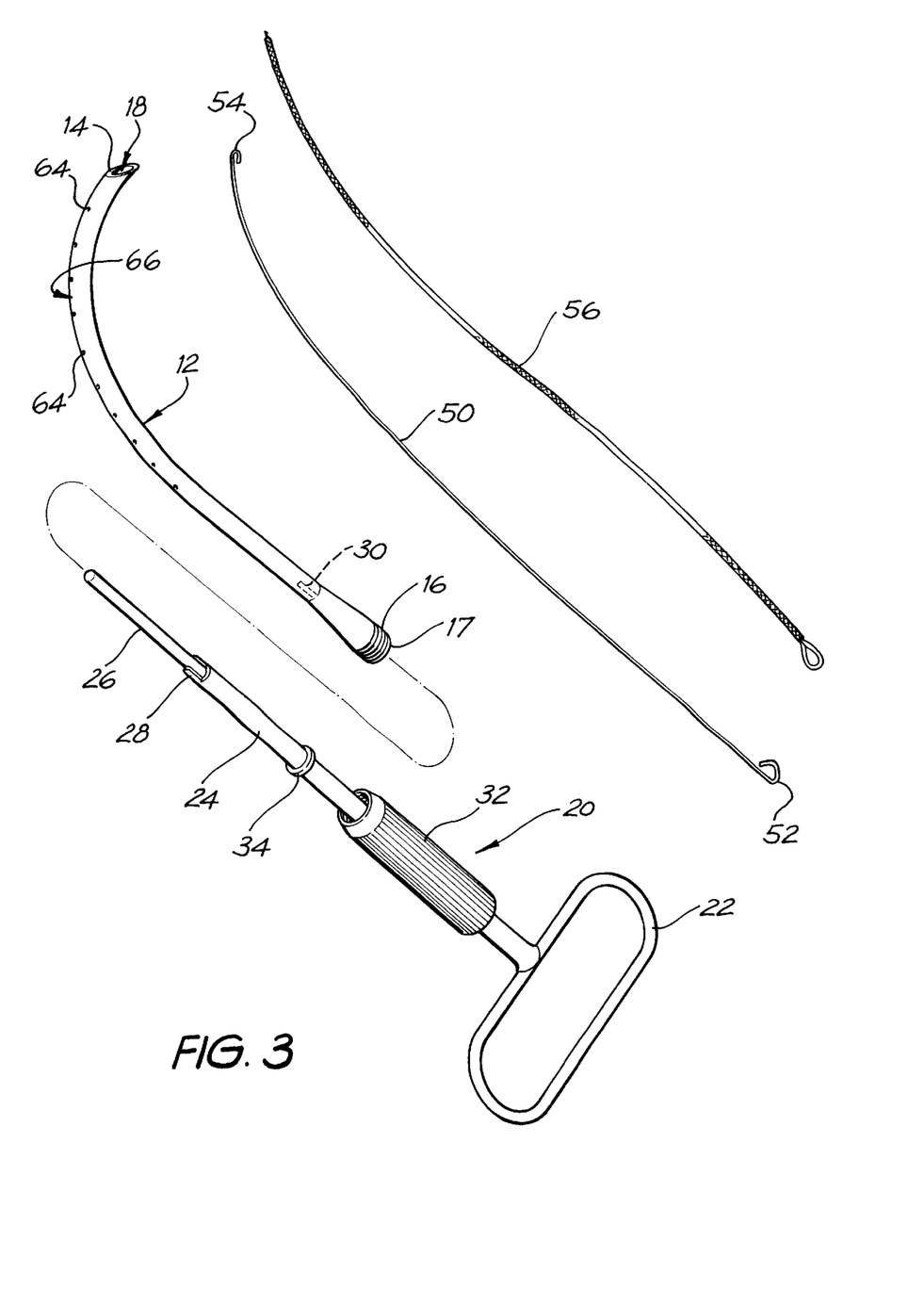
FIG. 3 shows an exploded perspective view of the elements required to perform an operation using the surgical instrument of the invention.

The instrument 10 includes a curved shaft 12 having a cutting tip 14 formed on the leading edge thereof and having a handle attachment arrangement 16 formed adjacent the opposite end 17 thereof. The cutting tip 14 is cut at an angle to the shaft axis, as shown clearly in the drawings, and the exact configuration of the cutting tip will be described in more detail here below. The shaft 12 is hollow defining an internal passage 18 the purpose of which is described in more detail below.

A handle 20 is connectable to the end 17 of the shaft, the handle 20 including a handle portion 22 which will be gripped, in use, by a surgeon performing a surgical procedure with the instrument 10. The handle 20 also includes a shaft portion 24 having a reduced diameter leading end 26 and interlocking formations 28 which engage with corresponding interlocking formations 30 formed on the interior surface of the passage 18. The engagement of the interlocking formations 28 and 30 are designed to ensure that the handle is non-rotatably connectable to the shaft 12 so that the surgeon is able to manipulate the direction of the shaft during insertion of the shaft into the body cavity by carefully twisting on the handle 22 during the procedure. A union nut 32 is slidable along the shaft portion 24 and is shown in FIG. 3 in a retracted position. An annular collar 34 is formed on the shaft portion 24 of the handle. When the reduced diameter portion 26 of the handle is fully inserted into the shaft 12 the collar 34 will butt up against the end 17 of the shaft and the union nut 32 will screw onto the threads 16 to securely hold the handle 20 to the shaft 12. To remove the handle from the shaft 12 the union nut 32 will be unscrewed from the threads 16 allowing the handle to be withdrawn from the shaft 12. It is important that this procedure is relatively simple to do since the handle will typically be removed from the shaft 12 during the course of the operation whilst the shaft 12 remains located within the patient. Thus, the union nut 32 will finger tightenable and loosenable.

It will be noted, particularly from FIG. 3, that the shaft 12 is of arcuate shape and is most significantly curved in the portion thereof adjacent the leading end 14 thereof. The shape of the shaft is selected so that the shaft is able to pass through an anterior surface of the vaginal wall behind the pubis to emerge through the abdominal wall. The radius of curvature is selected with this intended purpose in mind. As the shaft is inserted through the body cavity, around the pubis, the leading end of the shaft will tend to hug the pubis, with the sharp point staying remote from the bladder.

The portion of the shaft adjacent the handle is thus relatively straight whereas the leading portion of the shaft is significantly more curved. The curvature is in a single plane, that is, in use, the plane of the curvature will be substantially co-planar with the sagittal plane of the patient.

The cutting tip 14 is cut at an angle to the axis of the shaft, the tip lying in a plane which is perpendicular to the aforementioned plane of curvature. The leading point 36 of the cutting tip is located on the radially inner side 38 of the curved shaft with the remaining portion of the cutting tip sloping backwardly from that point 36 at an acute angle to the shaft axis 40. The cutting tip 14 lies in a plane which is at an acute angle to the shaft axis 40, the angle α being between 20° and 70°, but preferably approximately 45°. The shape of the tip, and specifically the point 36 being on the radially inner side thereof, will tend to keep the sharp leading end of the tip away from the bladder, thereby reducing the possibility of the point 36 rupturing the bladder. The angle of the cut will tend to push the bladder away from the point 36, further avoiding the possibility of rupture.

Although in this specification reference has been made to the cutting tip being "cut" at an angle to the shaft axis it will be understood that the manufacturing process does not require an actual cutting operation, but any manufacturing process which provides a surgically sharp angled cutting tip is to be considered as falling within the scope of the term "cut".

Figure 4:
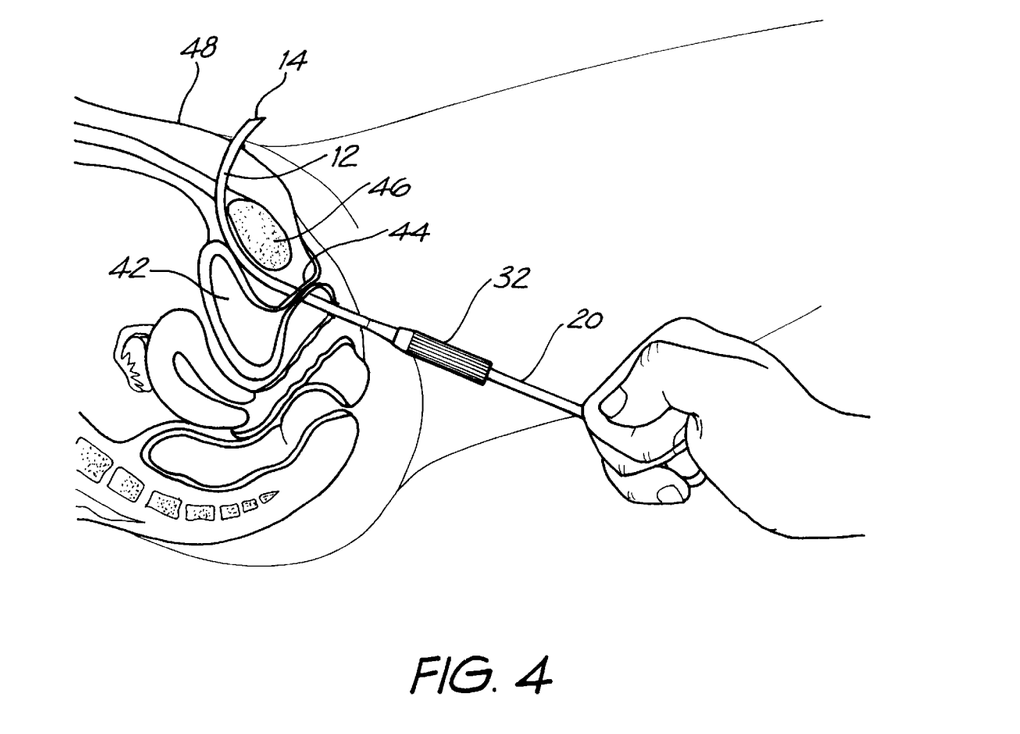
FIGS. 4–6 show the manner in which the surgical instrument is used in practice in different stages of an operation.
Figure 5:
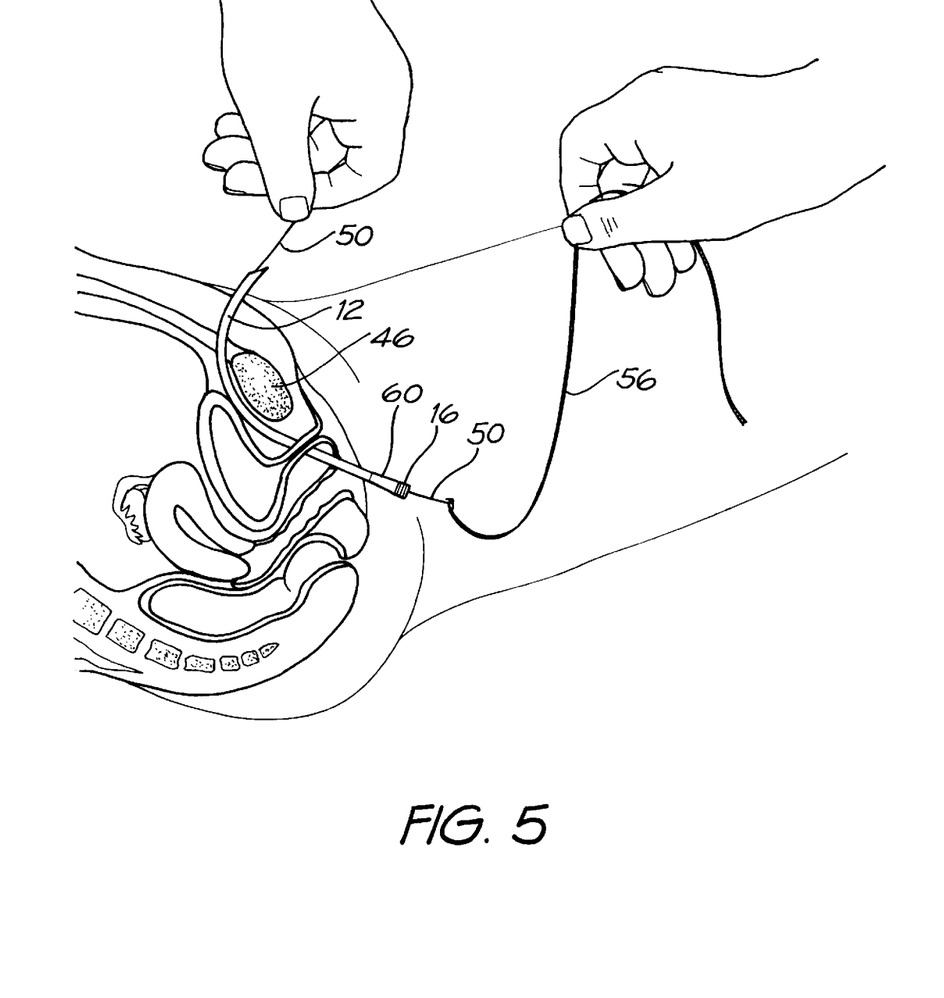
Figure 6:
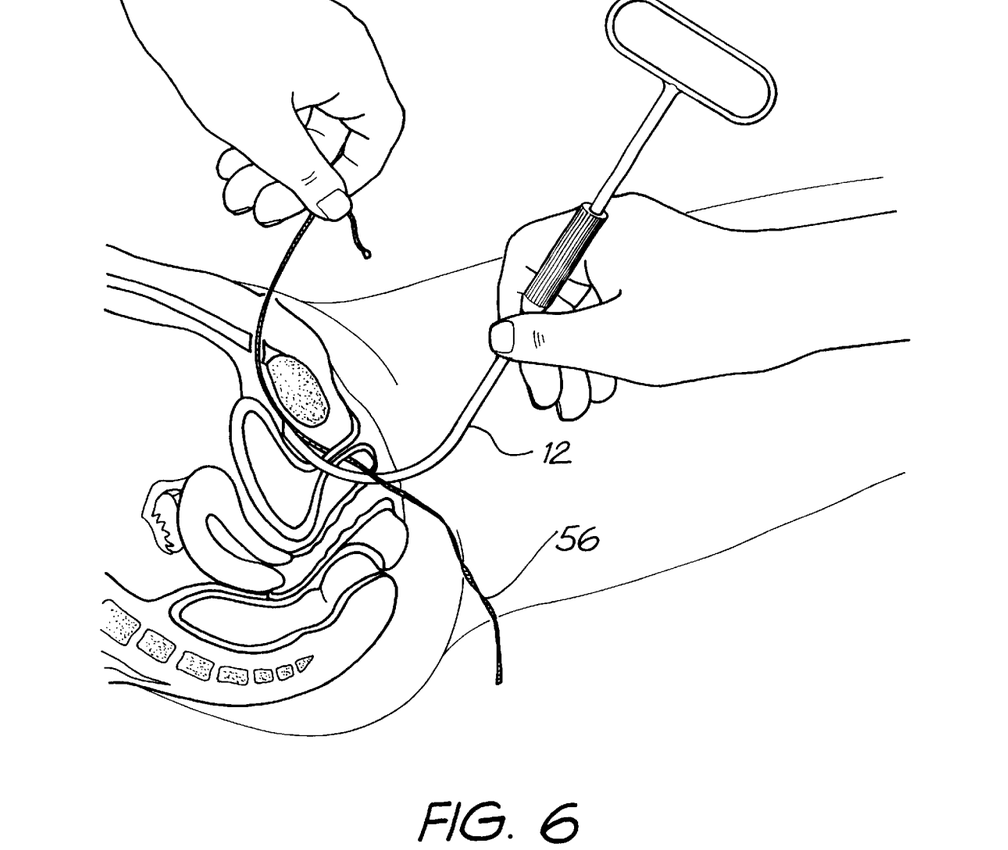

In use, at the start of the procedure the shaft 12 will be connected to the handle 20 in the manner described above and the shaft will be inserted into a patient typically through the vagina from a position inwards from the urethro vesical junction, the cutting tip passing into the body cavity so as to pass to one side of the urethra 44 between the bladder 42 and the pubis 46. The cutting tip will then pass out of the abdominal wall 48. The shaft, in its fully inserted position, is shown in FIG. 4 of the drawings.

Where it is desired to conduct the operation using a two incision procedure, two para-urethral vagina incisions will be made at or very near each anterior sulcus of the vagina. A tunnel will then be formed by blunt dissection between the urethra and the vaginal wall, the tunnel extending between the two para-urethral incisions. Typically the two incisions and the tunnel will be formed prior to the first insertion of the shaft into the patient's body cavity.

After the shaft has been fully inserted, the handle 20 is removed from the shaft 12 whilst the shaft 12 is retained, for the time being in the body cavity. A threading element 50 is passed through the internal passage of the shaft in the manner indicated in FIG. 5 of the drawings. It is important to note that the threading element 50 may be passed into the shaft 12 from either end of the shaft 12. The threading element 50 has a small gripping portion 52 on one end thereof and a hook 54 on the opposite end thereof. The hook 54 is used to grip a filamentary element 56 and the filamentary element 56 is provided with a loop 58 for this purpose. The filamentary element 56 will typically be made from a material such as "Prolene"(™) or "Vipro"(™) which are manufactured by Ethicon Inc. The threading element 50 will then be drawn out of the shaft 12 pulling with it the filamentary element 56 to thereby draw the filamentary element 56 through the hollow shaft 12. When the filamentary element 56 is fully in position the shaft 12 will be withdrawn from the patient. Once again, it is important to note that the shaft 12 may be withdrawn from the patient from either the abdominal side of the patient or the vaginal side of the patient and the shaft is specifically shaped and configured for this purpose. The threading element 50 may, of course, be used to push the filamentary element through the shaft.

It will be noted that the shaft 12 has a tapered portion 60 adjacent the trailing end 17 thereof which provides a smooth transition between the cylindrical central portion of the shaft and the threaded end 17 thereof. This tapered portion 60 is specifically designed to allow the shaft to be drawn in a forward direction through the patient without causing any further tissue damage to the patient. The taper angle of the tapered position should be small, that is, about 5° or less. Other connection arrangements are possible which would result in substantially no increase in diameter. An internal screw thread arrangement will, for example, be possible. Other alternatives are discussed below.

Where the two incision process is preferred, the vaginal end of the filament will be guided through the aforementioned tunnel and out of the second incision. The handle will then be re-attached to the shaft and the shaft inserted back into the patient's body, on the opposite side of the urethra to again pass between the bladder 42 and the pubis 46 and out of the abdomen 48. Thereafter, the handle will be removed from the shaft, and, working from the abdomen side of the patient, the threading element will be fed through the hollow shaft. The hook on the end of the threading element will then be used to capture the filament and the draw the filament through the hollow shaft to emerge out of the abdomen side of the patient. The hollow shaft will then be removed from the abdomen side of the patient, leaving a U-shaped loop of filamentary material in the patient which extends around the urethra. This procedure is not possible with the prior art instruments referred to above.

In most procedures the shaft will be withdrawn from the patient from the abdominal side during this second stage of the operation. Where it is withdrawn from the abdominal side of the patient the end 17 of the shaft will need to pass through the patient which is why the smooth and slightly tapered section 60, referred to above, is provided and also the fact that the threads 16 are not of significantly larger diameter than the central or cylindrical portion of the shaft.

Once the filamentary element has passed twice through the patient's body cavity the free ends of the loop thus created will be cut off. A U-shaped loop will be left, typically permanently, in the patient's body, forming an artificial ligament around the urethra, and significantly improved urinary control will be achieved for the patient.

The filament may be either permanently left within the patients body or may at some stage thereafter be removed, these two options being discussed in the prior art referred to above.

It will be noted that the shaft 12 is provided with a series of apertures 64 which pass through the wall of the shaft into the interior passage 18. Those apertures 64 are located on the radially outer side 66 of the curved portion of the shaft 12, that is, the side of the shaft 12 would face towards the patient's bladder during the aforementioned surgical procedure.

During the course of the aforementioned procedure, the shaft passes very close to the patient's bladder but it is important that the bladder is not ruptured or damaged in any way during the procedure. With prior art devices there is often no indication that such damage to the bladder might have occurred during the procedure, particularly where the rupture caused by the procedure is small.

It is found that with the apertures 66 located along the length of the shaft, should any such damage occur, urine will leak from the bladder through the apertures 64 and out through the end 17 of the shaft. A surgeon will thus immediately become aware that bladder damage has occurred. This is considered to be a significant improvement over prior art devices which do not provide any such damage indicating arrangement.

Figure 7:
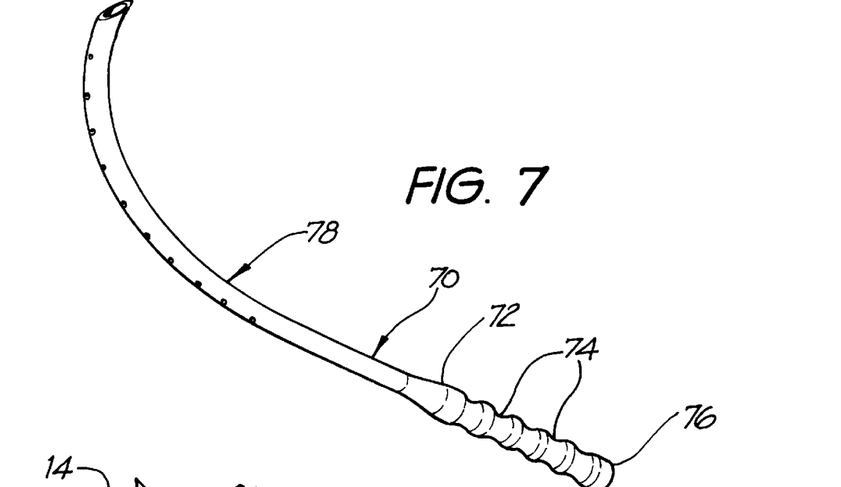
FIG. 7 shown an alternative embodiment of the invention.

It should be noted that it is an important aspect of the invention that the shaft be removable from the patient from the abdomen side of the patient. Where the instrument has a handle secured thereto it will, of course, be necessary to first remove the handle from the shaft before abdominal removal can take place. However, as shown in FIG. 7, it is not essential that the handle be removable from the shaft. The shaft 70 shown in FIG. 7 has a handle end 72 having a series of annular groves 74 formed therein which the surgeon can grip when performing the aforementioned operations. The passage through the shaft 70 will extend all the way through the handle portion 72 emerging at the trailing end 76 of the shaft. Thus, the threading element 50 and the filamentary element 56 will be useable with the shaft 70 in the same manner as described above but the handle removal step will no longer be necessary.

In the embodiment shown in FIG. 7 the handle portion 72 has a slightly wider diameter than the shaft portion 78 to allow slightly better grip of the shaft 70. However, it will be possible to form the handle portion 72 with exactly the same diameter as the shaft portion 78 should it be found that slightly wider diameter of the handle portion 72 causes difficulty in passing the instrument through a patient.

Clearly, different forms of handle grip arrangements will be possible and specifically envisaged is an arrangement in which longitudinally aligned gripping grooves or ridges are formed in the handle portion 72.

The device shown in FIG. 7 is advantageous in that the device can be made far less expensive since it is of unitary construction. Also, no disconnection of the device is necessary mid-way through the surgical procedure. However, the twisting forces which can be applied to the device will be reduced on account of the inferior turning forces which can be applied to the shaft by not having a laterally extending handle on the end thereof.

Figure 8:
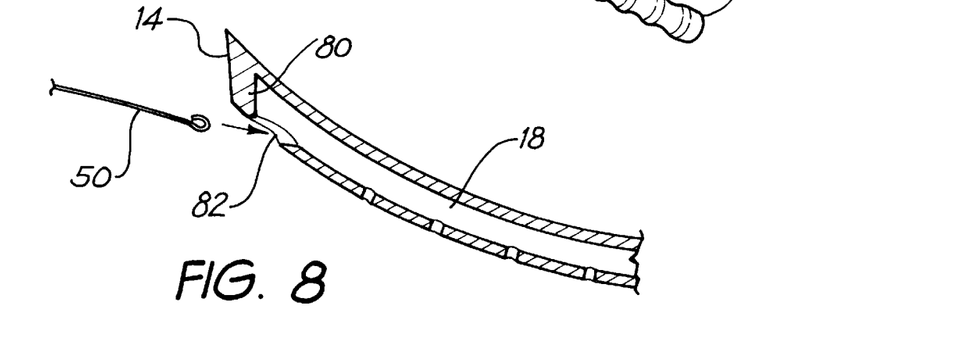
FIG. 8 shows an alternative version of the leading end of the surgical instrument of the invention.

It is not, of course, essential that the internal passage way extends all the way to the end of the leading of the shaft. Indeed, as shown in FIG. 8, it might in some instances be preferable for the leading end 14 of the shaft to be closed off with an end wall 80 and for a lateral opening 82 to be formed through the side wall of the shaft just adjacent the leading end 14. A lateral opening 82, of the type shown in FIG. 8, will still allow the threading element 50 to be inserted into the interior passage 18 of the shaft but the end wall will provide a sheer leading face for the instrument, thereby ensuring minimum resistance to the instrument as it passes through the body cavity. Clearly, the opening 82 can be used exactly in the manner described above to draw the filament through the passage 18. However, for certain procedures it may be found that the open end, as shown in FIG. 2, might be more difficult to pass through body tissue.

Figure 9:
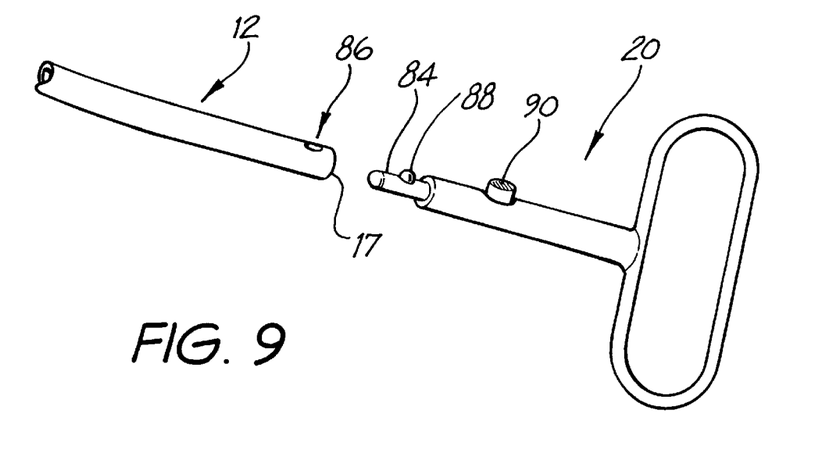
FIG. 9 shows an alternative version of the connection arrangement between the shaft and the handle.

Also, as mentioned above, it is not essential that the handle 20 is connectable to the shaft 12 by means of a threaded connection. Other forms of connection such as a bayonet connection or even some form of interlocking groove connection might be equally satisfactory, provided engagement and disengagement between the shaft and handle are made to be relatively straight forward and easily achieved. One form of alternative mechanical connection is shown in FIG. 9 of the drawings. As shown, the handle 20 has a reduced diameter stub 84 on the leading end thereof which is sized to fit neatly into the interior passage 18 in the shaft 12. The shaft 12 is provided with a small hole 86 through the wall of the shaft just adjacent the rearward end 17. An interlocking, retractable pin 88 is provided in the stub 84 and is operable by means of a retraction button 90 located somewhat down the shaft of the handle 12. Pressure on the retraction button 90 will cause the pin 88 to retract. Thus, to engage the handle 20 with the shaft 12 the stub 84 will be inserted into the passage 18 in the shaft 12 and when properly so inserted the pin 88 will locate in the hole 86, thereby non-rotatably locking the handle 20 to the shaft 12. When it is desired to remove the handle 20 from the shaft 12 the button 90 will be depressed causing the pin 88 to retract and allowing the handle 20 to be removed from the end 17 of the shaft. Clearly other forms of interlocking arrangements which are mechanically operable from the handle side of the instrument can be employed.

Figures 10, 11, 12:
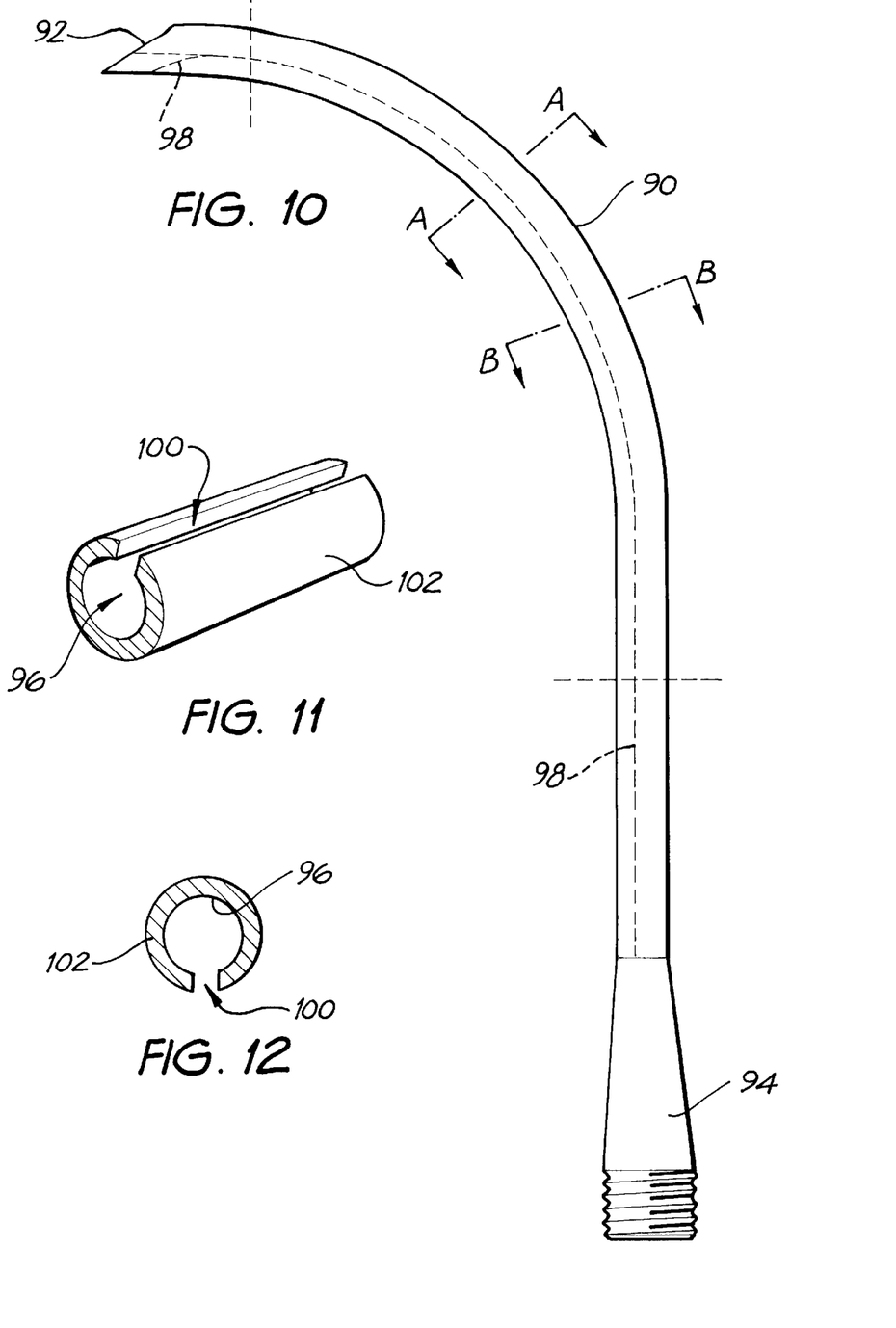
FIG. 10 shows a side view of an alternative embodiment of surgical instrument according to the invention.
FIG. 11 shows a perspective view of that portion of the FIG. 10 instrument between lines AA and BB.
FIG. 12 shows a sectional view along line AA of FIG. 10.

The instrument shown in FIG. 10 of the drawings is similar to that shown in the previous embodiments and comprises a generally hollow shaft 90 having a cutting tip 92 on one end thereof and handle means 94 on the opposite end thereof. The shaft 90 is of generally tubular construction having an internal passage 96 which may run the length of shaft 90 or, alternatively, may stop short of the ends of shaft 90 as indicated by dotted lines 98. A slot 100 is cut through the wall 102 of the shaft 90, the slot 100 being longitudinally aligned with the shaft axis, thereby forming a lateral passage out of the internal passage 96. The slot and passage are best shown in FIG. 11 of the drawings.

It is envisaged that the slot 100 will be formed on the radially inner side of the curved shaft 90.

It is envisaged that in certain circumstances it will not be essential to draw the filament longitudinally out of the shaft when the shaft is removed from a patient's body cavity. In some instances it may be possible to move the filament laterally out of the shaft, during the course of the procedure, thereby avoiding having to pull the shaft through the patient from the abdominal side of the patient. Where the second arm of the U-shaped loop of filamentary material is inserted around the urethra, provide this filamentary material can be moved laterally through the slot 100, so as to rest within the patient, then the shaft may be withdrawn from the vaginal side of the patient. This will require only single abdominal side incision. Indeed, it may be possible to perform the procedure from the vaginal side of the patient exclusively provided it is possible to cause a filamentary material to move laterally out of the internal passage 96 prior to the removal of the shaft from the patient.

Figure 13:
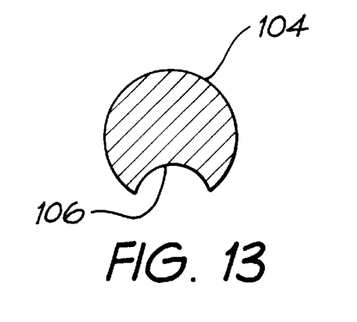
FIG. 13 shows a similar view to that of FIG. 12 but of a yet further alternative embodiment of the invention.
Figure 14:
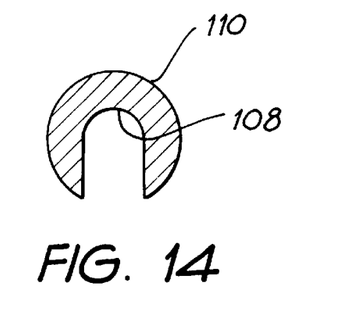
FIG. 14 shows a similar view to that of FIG. 12 of a yet further alternative embodiment of the invention.

FIG. 13 depicts an alternative version of the instrument. In this version the shaft 104 is formed of a solid material and a relatively shallow channel 106 is formed in one side thereof, the channel 106 extending either the full length of the shaft or at least a significant portion of the length of the shaft. The embodiment shown in FIG. 14 of the drawings is similar to that of FIG. 13 but the channel 108 is significantly deeper than the channel 106. Also, it will be noted that the shaft 110 shown in FIG. 14 is of non-circular cross sectional configuration.

Figure 15:
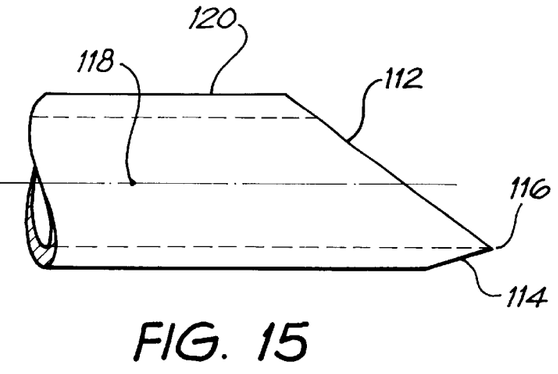
FIG. 15 shows a side view of an alternative version of the cutting tip of the invention.
Figure 16:
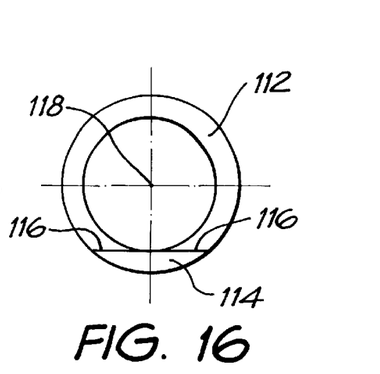
FIG. 16 shows an end view of the cutting tip shown in FIG. 15.

FIGS. 15 and 16 depict an alternative version of the cutting tip of the instrument. As shown in FIG. 15 and FIG. 16 the cutting tip is defined by two bevel surfaces, numbered 112 and 114, the surface 112 being the major surface and the surface 114 being a minor surface. Each of the bevel surfaces 112 and 114 are planar, the two surfaces intersecting along a line 116 which is perpendicular to the longitudinal axis 118 of the shaft 120 and forms the sharp leading end of the instrument. It is envisaged that the line 116 will be offset from the centre line 118 to the radially outer side of the curved shaft. This will mean that in the procedure referred to above the actual sharp tip of the instrument, that is, the edge forward at the intersection between the two bevel faces, will be nearer to the pubic bone than the bladder as the instrument is passed through the body cavity. Displacing the sharp edge away from the radially inner side of the shaft will ensure that the sharp edge tip does not either cut into or shave the pubic bone. The sharp edge tip will still, however, be remote from the bladder and the bevel face 112 will tend to push the bladder away from the edge 116 should the instrument pass close to the bladder during the procedure.

While the above detailed description has shown, described and pointed out fundamental novel features of the invention as applied to the embodiment discussed above, it will be understood that various omissions and substitutions and changes in the form and detail of the invention illustrated may be made by those skilled in the art, without departing from the spirit of the invention. The described embodiments are to be considered in all respects only as illustrative and not restrictive. The scope of the invention is, therefore, indicated by the appended claims rather than the foregoing description. The applicant does not concede that the prior art referred to herein forms part of the common general knowledge in the art in Australia.

What is claimed is:

1. A surgical instrument for use in placing an elongate filamentary element into a patient to treat female incontinence said instrument comprising:

an elongate shaft defining an internal passage, said shaft having a cutting tip formed on one end thereof and a handle formed on the other end thereof; the shaft including the handle being sized and shaped such that the shaft may be passed into and through a patient, the internal passage being provided to introduce a said elongate element into the patient whilst the instrument is located in a patient in use;

wherein the shaft has one of a longitudinally extending slot, a groove and a channel formed therein which extends at least part way along the length thereof and defines at least in part said internal passage.

2. A surgical instrument according to claim 1 wherein the handle comprises a shaft portion integrally formed on said shaft and a handle portion, which is non-rotatably connectable to said other end of the shaft.

3. A surgical instrument according to claim 1 wherein the shaft is generally arcuately curved.

4. A surgical instrument according to claim 1 wherein the shaft is tubular.

5. A surgical element according to claim 1 wherein said tube has a substantially uniform cross section along its entire length.

6. A surgical instrument according to claim 1 wherein said shaft is of generally tubular construction and has a longitudinally extending slot formed through the wall thereof.

7. A surgical instrument according to claim 1 wherein the cutting tip lies in a plane which is transverse and angled to the longitudinal axis of the shaft.

8. A surgical instrument according to claim 1 wherein the cutting tip lies in two intersecting planar bevel faces, said bevel faces intersecting along a line which is perpendicular to the longitudinal axis of the shaft.

9. A surgical instrument according to claim 8 wherein the line along which the two bevel faces intersect is laterally offset to one side of the longitudinal centreline of the shaft.

10. A surgical instrument according to claim 1 wherein the internal passage terminates rearward of the cutting tip.

11. A surgical instrument for use in placing an elongate filamentary element into a patient to treat female incontinence said instrument comprising:

an elongate shaft defining an internal passage, said shaft having a cutting tip formed on one end thereof and a handle formed on the other end thereof, the shaft including the handle being sized and shaped such that the shaft may be passed into and through a patient, the internal passage being provided to introduce a said elongate element into the patient whilst the instrument is located in a patient in use;

wherein the shaft has a series of apertures spaced apart along the length of at least part of the shaft, said apertures passing through a wall of the shaft into said internal passage.

12. A surgical instrument for use in placing a filamentary element into a female patient so as to form a sling or loop around the urethra extending over the back of the pubic bone to the abdominal wall, said instrument comprising:

a generally arcuately curved tubular shaft defining an internal passage, said shaft having a cutting tip formed on one end thereof and a handle attachment formed on the other end thereof;

a handle, non-rotatably and removably connected to the handle attachment of the shaft and being selectively disconnectable from the shaft during surgical procedures; and a flexible threading element a adapted to be inserted into and through said internal passage and adapted to be used to draw one end of a said filamentary element through said internal passage;

wherein the shaft has a series of apertures spaced apart along the length of at least part of the shaft, said apertures passing through a wall of the shaft into said internal passage.

13. A surgical instrument for use in placing a filamentary element into a female patient so as to form a sling or loop around the urethra over the back of the pubic bone, to the abdominal wall, said instrument comprising:

a generally arcuately curved shaft defining a longitudinally extending internal passage, said shaft having a cutting tip formed on one end thereof and a handle attachment formed on the other end thereof;

a handle, non-rotatably connectable to the handle attachment of the shaft; and a flexible threading element insertable into and through said internal passage from either end of said shaft and adapted to be used to draw one end of a said filamentary element through said internal passage;

said tubular shaft being curved so that the shaft lies substantially in a single plane;

wherein the shaft has one of a longitudinally extending slot, a groove and a channel formed therein which extends at least part way along the length thereof and defines at least in part said internal passage;

the cutting tip at least in part being of planar bevel shape so as to lie in a plane perpendicular to said single plane and at an acute angle to the shaft axis.

14. A surgical instrument according to claim 13 wherein the acute angle is between 20° and 70°.

15. A surgical instrument according to claim 14 wherein the acute angle is approximately 45°.

16. A surgical instrument according to claim 13 wherein the cutting tip lies in two intersecting planar bevel faces, said bevel faces intersecting along a line which is generally perpendicular to the longitudinal axis of the shaft.

17. A surgical instrument according to claim 13 wherein the handle attachment comprises screw threads formed on the radially outer surface of the shaft.

18. A surgical instrument according to claim 17 wherein the shaft tapers divergently towards the handle attachment so as to form a smooth transition between a cylindrical central portion of said shaft and said handle attachment.

19. A surgical instrument according to claim 13 wherein the interior surface of said internal passage at or towards said other end of the shaft includes one of a notch and a detent formation with which said handle engages to provide said non-rotatable connection.

20. A surgical instrument according to claim 13 wherein said handle comprises a hand engagable portion which is significantly wider than said shaft, and an elongate connection portion, adapted to be axially aligned with said other end of the shaft when the handle and the shaft are operatively connected.

21. A surgical instrument according to claim 20 wherein said elongate connection portion has a distal end of reduced diameter adapted to be inserted into the internal passage of the shaft.

22. A surgical instrument according to claim 20 wherein said shaft is formed with screw threads and the handle includes an annular flange on said elongate connection portion which is adapted to engage against said other end of the shaft, and a union nut captively held on said elongate connection portion between the annular flange and the handle portion, and slidable on said shaft portion, said union nut adapted to engage with said screw threads in order to hold the shaft and handle together.

23. A surgical instrument according to claim 13 wherein the shaft has a generally arcuate portion towards said one end thereof, and a generally straight portion towards said other end thereof.

24. A surgical instrument according to claim 13 having at least one aperture passing through the wall thereof between the internal passage and the exterior of the shaft.

25. A surgical instrument according to claim 24 wherein there are a series of apertures spaced apart along the length of the shaft which are located on the radially outer side of said curve shaft.

26. A surgical element according to claim 13 wherein said tube has a substantially uniform cross section along its entire length.

27. A surgical instrument comprising:

a. a hollow curved tubular shaft defining an interior passage and having an acutely cut first end forming a sharp point and a handle that is non-rotatable and is further detachably connectable to the other end;

b. a flexible threading element which is at least as long as the shaft, the threading element and the shaft being adapted to be used, when the handle is detached, to draw a filamentary element through the internal passage through the shaft; and c. the shaft is shaped and configured to be used to pass a filamentary element through a female patient through an anterior wall of the vagina to an anterior wall of the abdomen through the wall thereof into the interior passage wherein the filamentary element forms a sub urethral sling, in part extending over the back of the pubic bone to the abdominal wall.

28. A surgical instrument for use in placing a filamentary element into a female patient so as to form a sling or loop around the urethra extending over the back of the pubic bone to the abdominal wall, said instrument comprising:

a generally arcuately curved tubular shaft defining an internal passage, said shaft having a cutting tip formed on one end thereof and a handle attachment formed on the other end thereof;

a handle, non-rotatably and removably connected to the handle attachment of the shaft and being selectively disconnectable from the shaft during surgical procedures; and a flexible threading element a adapted to be inserted into and through said internal passage and adapted to be used to draw one end of a said filamentary element through said internal passage;

wherein the shaft has one of a longitudinally extending slot, a groove and a channel formed therein which extends at least part way along the length thereof and defines at least in part said internal passage.

29. A surgical instrument for use in placing a filamentary element into a female patient so as to form a sling or loop around the urethra over the back of the pubic bone, to the abdominal wall, said instrument comprising:

a generally arcuately curved shaft defining a longitudinally extending internal passage, said shaft having a cutting tip formed on one end thereof and a handle attachment formed on the other end thereof;

a handle, non-rotatably connectable to the handle attachment means of the shaft; and a flexible threading element insertable into and through said internal passage from either end of said shaft and adapted to be used to draw one end of a said filamentary element through said internal passage;

said tubular shaft being curved so that the shaft lies substantially in a single plane;

wherein the shaft has a series of apertures spaced apart along the length of at least part of the shaft, said apertures passing through a wall of the shaft into said internal passage; and the cutting tip at least in part being of planar bevel shape so as to lie in a plane perpendicular to said single plane and at an acute angle to the shaft axis.

30. A method of introducing a filamentary element into a female patient so as to form a sling or loop extending around the urethra to the abdominal wall, said method including the steps of:

a) inserting a generally arcuately curved shaft having a longitudinally extending internal passage into the patient through a first incision in the anterior surface of the vaginal wall, so as to pass on one side of the urethra between the pubis and the bladder and out of the patient through the abdominal wall;

b) passing a threading element through the internal passage from one or other end thereof so that the distal end of the threading element passes out of the remote end of the internal passage;

c) attaching a filamentary element to the distal end of the threading element and drawing the filamentary element through the internal passage with the threading element;

d) withdrawing the hollow shaft from the patient whilst leaving the filamentary element in position in the patient;

e) inserting the shaft into the patient through the anterior surface of the vaginal wall, so as to pass on the other side of the urethra between the pubis and the bladder;

f) drawing the filamentary element into position through the internal passage using the threading element; and g) withdrawing the shaft from the patient whilst leaving the filamentary element in position thereby forming a loop which extends around the urethra to the abdominal wall.

31. A method according to claim 30 in which the filament is drawn in steps c) and f) through the patient by pulling the filamentary element through the patient from the abdominal side of the patient.

32. A method according to claim 30 or 31 prior to conducting step e) a second incision is made through the anterior surface of the vaginal wall and a tunnel is created between the first and second incisions, and the end of the filamentary element adjacent the vagina is passed through said tunnel and out of said second incision.

33. A method according to claim 30 wherein the shaft is withdrawn from the patient from the abdominal side of the patient.

* * * * *